US008249265B2

(12) United States Patent
Shumard

(10) Patent No.: US 8,249,265 B2
(45) Date of Patent: Aug. 21, 2012

(54) METHOD AND APPARATUS FOR ACHIEVING ACTIVE NOISE REDUCTION

(76) Inventor: Eric L. Shumard, Indianapolis, IN (US)

( * ) Notice: Subject to any disclaimer, the term of this patent is extended or adjusted under 35 U.S.C. 154(b) by 1286 days.

(21) Appl. No.: 11/856,406

(22) Filed: Sep. 17, 2007

(65) Prior Publication Data

US 2008/0069368 A1 Mar. 20, 2008

Related U.S. Application Data

(60) Provisional application No. 60/825,734, filed on Sep. 15, 2006.

(51) Int. Cl.
*A61F 11/06* (2006.01)

(52) U.S. Cl. ......................... 381/71.1; 381/94.1; 381/95

(58) Field of Classification Search ................. 381/71.6, 381/71.1, 71.11, 71.12, 94.1, 94.9, 95, 111, 381/120, 122, 335
See application file for complete search history.

(56) References Cited

U.S. PATENT DOCUMENTS

| | | | | |
|---|---|---|---|---|
| 3,908,095 | A | 9/1975 | Jinsenji | |
| 3,987,245 | A | 10/1976 | Fasen et al. | |
| 5,001,763 | A | 3/1991 | Moseley | |
| 5,134,659 | A | 7/1992 | Moseley | |
| 5,668,883 | A | 9/1997 | Abe et al. | |
| 6,078,672 | A | 6/2000 | Saunders et al. | |
| 6,118,878 | A | 9/2000 | Jones | |
| 6,175,634 | B1 * | 1/2001 | Graumann | 381/94.1 |
| 6,597,792 | B1 | 7/2003 | Sapiejewski et al. | |
| 7,043,028 | B2 * | 5/2006 | Leske et al. | 381/59 |
| 7,065,219 | B1 | 6/2006 | Abe et al. | |
| 7,042,476 | B2 | 7/2006 | White et al. | |
| 7,466,838 | B1 * | 12/2008 | Moseley | 381/370 |
| 2003/0095680 | A1 * | 5/2003 | Kim et al. | 381/409 |
| 2003/0235318 | A1 | 12/2003 | Bharitkar et al. | |
| 2004/0136543 | A1 * | 7/2004 | White et al. | 381/74 |
| 2005/0249355 | A1 | 11/2005 | Chen et al. | |
| 2007/0053528 | A1 * | 3/2007 | Kim et al. | 381/107 |
| 2008/0037801 | A1 * | 2/2008 | Alves et al. | 381/71.6 |

OTHER PUBLICATIONS

Bharitkar, Kyriakakis, "Selective Signal Cancellation for Multiple-Listener Audio Applications Using Eigenfilters," IEEE Transactions on Multimedia, Sep. 2003, pp. 329-337, vol. 5, No. 3.
Habib, Kepesi, "Open Issues of Active Noise Control Applications," IEEE, 2007, Signal Processing and Speech Communication Laboratory, TU Graz, Austria.
Kuo, Sen; Morgan, Dennis, "Active Noise Control Systems," 1996, Ch. 2, pp. 17-51, Ch. 6-7, pp. 186-240.

* cited by examiner

*Primary Examiner* — Vivian Chin
*Assistant Examiner* — Friedrich W Fahnert
(74) *Attorney, Agent, or Firm* — Ice Miller LLP

(57) ABSTRACT

A system and method for actively changing the sound perceived by listeners in an audio environment. A single transducer is used as both a sensing microphone and as an output driver. In one embodiment, the invention is implemented as an active noise cancellation system. The sensed noise signals are phase shifted to provide a cancellation effect, combined with the desired audio program signals, and output to the transducer, thereby reducing the level of unwanted noise heard by they listener. In other embodiments, the system can be used to sense the frequency response of a listening room and make appropriate equalization adjustments to the output.

18 Claims, 6 Drawing Sheets

METHOD AND APPARATUS FOR ACHIEVING ACTIVE NOISE REDUCTION

RELATED APPLICATION

This application claims priority from provisional application Ser. No. 60/825,734, filed Sep. 15, 2006, the contents of which are incorporated herein by reference.

FIELD OF INVENTION

The present invention relates to active noise cancellation systems for audio listening applications.

BACKGROUND

In audio listening applications, it is normally desirable to minimize the amount of background noise heard by the user. Methods for achieving such reduction fall into two main categories, passive and active. Passive noise reduction is accomplished by acoustically isolating the listener from the external noise source through the use of insulation or other sound blocking materials. However, the results are often unsatisfactory due to the difficulty of effectively blocking frequencies in the lower range of the audible spectrum.

Active noise reduction systems use the principle of phase reversal to cancel out unwanted signals. In these systems, a microphone is used to sense external background noise. This signal is then phase shifted to create a cancellation signal and added to the intended audio program signal sent to the speaker. The cancellation signal combines with the noise and effectively reduces or eliminates the level of unwanted noise perceived by the listener.

One shortcoming to active noise cancellation systems currently available is that a dedicated microphone must be incorporated to sense the noise heard by the user. For example, noise cancelling headphone sets will typically employ one microphone per ear piece and have their own power supply which energizes an electronic circuit to process the signal from the microphones and generate the cancellation signal. This additional circuitry increases the size and cost of such units and limits their marketability to consumers. Additional problems are presented due to the distance between the sensing microphone, the speaker, and the listener's ear, making cancellation of higher frequency noise signals problematic.

SUMMARY

The present invention solves the problems inherent in the prior art by capitalizing on the established principle that most speakers will act as microphones to a certain degree. Even though most speakers are designed for optimum output performance, external sound will interact with the speaker diaphragm to induce a corresponding electrical signal at the speaker terminals. This signal can then be isolated from the output signal through various processing techniques known in the art, inverted, and sent back to the speaker to create the noise cancelling effect.

By obtaining the noise signal from the output speaker itself, the need for a dedicated microphone to sense the external noise is eliminated. In one form, the noise cancelling circuitry can be incorporated into a source device, such as a personal music player. The user is then free to operate the device with a variety of standard headsets or speaker systems. The additional processing circuitry should add only a small cost to the driving device while still providing an acceptable level of noise reduction for the user. Another advantage of this approach is that there is no longer a physical distance between the output speaker and the microphone, thereby increasing the range of frequencies amenable to cancellation.

In another form, the present invention can be incorporated into a larger music source device, such as a home theater system. Again, the level of background noise penetrating the listening room from other parts of the house could be obtained from the output speakers and used to create a similar noise cancelling effect without the need for a dedicated measurement microphone. The invention could further be used in such systems to obtain the room frequency response data directly from the output speakers for use in corrective equalization techniques.

This summary is provided to introduce a selection of concepts in a simplified form that are described in further detail in the detailed description and drawings contained herein. This summary is not intended to identify key features or essential features of the claimed subject matter, nor is it intended to be used as an aid in determining the scope of the claimed subject matter. Yet other forms, embodiments, objects, advantages, benefits, features, and aspects of the present invention will become apparent from the detailed description and drawings contained herein.

DETAILED DESCRIPTION

Figure 1:
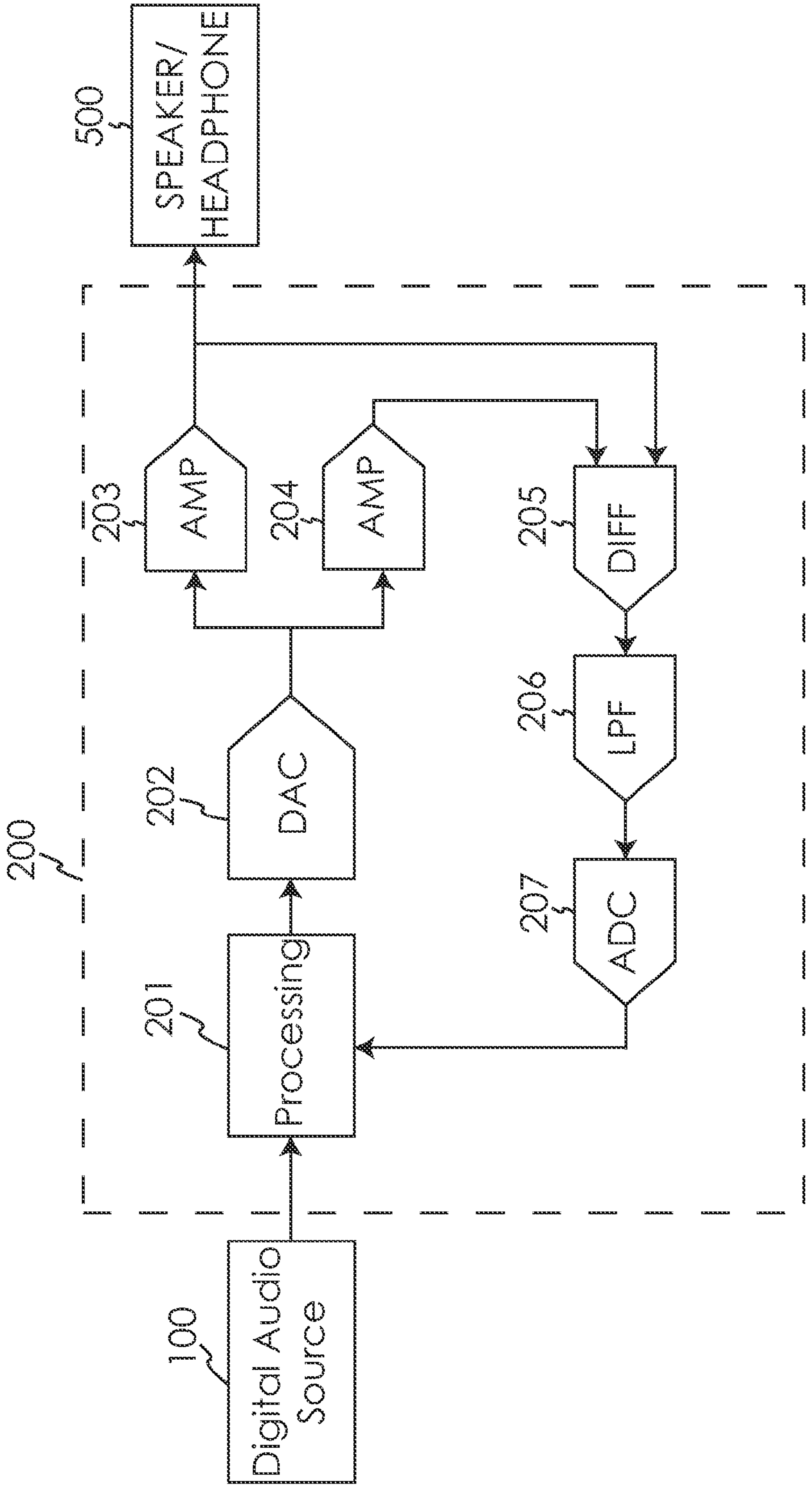
FIG. 1 is a schematic diagram depicting a digital implementation of the present invention.

For the purposes of promoting and understanding of the principles of the invention, reference will now be made to the embodiment illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. The present invention can be implemented with various mixtures of analog and digital circuitry.

Figure 2:
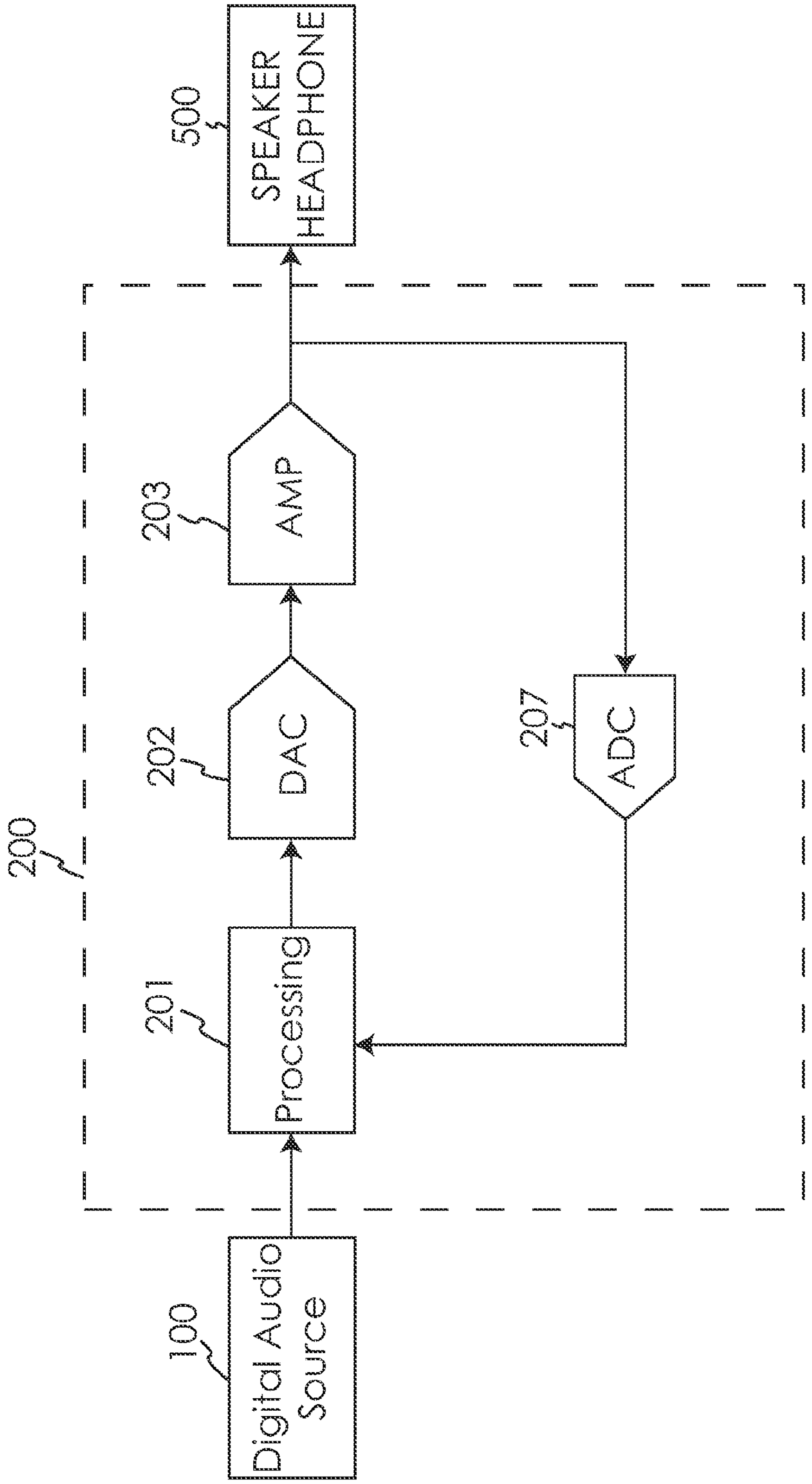
FIG. 2 is a schematic diagram depicting a hybrid analog-digital implementation of the present invention.

FIG. 1 illustrates a hybrid analog-digital implementation and FIG. 2 illustrates a digital implementation of the present invention. Note that these illustrations represent the implementation for a single channel and for a typical stereophonic audio system this circuitry is replicated for each channel. It is possible to combine information from both stereo channels to aid in canceling the external noise as the external noise will typically exist in both channels.

Referring to FIG. 1, digital audio source 100 is typical of those found in personal musical players or home theater systems and connects original audio program material to processing unit 201. Processing unit 201 is a digital processor capable of performing various signal manipulating functions, including, but not limited to, equalization, level adjustment, filtering, and phase shifting. The output of processing unit 201 is directed to digital to analog converter (DAC) 202, also typically found in most digital music players. The output of DAC 120 is connected to the input of amplifiers 203 and 204. The output of amplifier 203 is connected to both speaker/headphone 500 (which can be any speaker or device containing one or more speakers, such as a pair of headphones or one or more speaker enclosures, to name just a few non-limiting examples) and one input of difference amplifier 205. The output of amplifier 204 is connected to the remaining input of difference amplifier 205. The output of difference amplifier 205 passes through low pass filter 206 before being converted to digital form by analog to digital converter (ADC) 207 and connected to processing unit 201. The components connected between the digital audio source 100 and headphone 500 are collectively referred to as control unit 200.

Amplifier 204 provides a reference analog source signal which can be subtracted from the signal present at the junction between the amplifier 203 and the headphone 500. Because the headphone 500 functions as both a speaker to broadcast the analog source signal produced by amplifier 203 and as a microphone to produce a signal representing the combined broadcast analog source and noise existing at the headphone 500, removing the analog source signal from the signal produced by the headphone 500 will leave a signal representing the external noise measured at the headphone 500. Difference amplifier 205 produces an analog signal which is formed by subtracting the reference signal from amplifier 204 from the signal measured at headphone 500. Therefore, the output of difference amplifier 205 contains only the noise signal from the headphone 500 acting as a microphone, i.e., the signal produced by external sound which has not been canceled. Optionally, a programmable termination or programmable gain may be applied to the output of amplifier 204 to match the termination of the specific attached headphone 500. Low-pass filter 206 is typically set to suppress signals with frequencies above a few KHz. In practice, only signals up to a few KHz are able to be canceled because only sounds which have wavelengths on the order of or larger than the relevant length scales of a system are amenable to cancellation. The relevant length scales are determined by the distance between the microphone, speaker, and the ear. Since the microphone and speaker elements are physically coincident for this method (the microphone is the speaker), it is possible to achieve cancellation at higher frequencies than other methods which have physical separation between the microphone and speaker elements.

The processing element 201 generates a scaled and inverted version of the noise signal from ADC 207, adds it to the signal from the digital audio source 100 and sends it to digital to analog converter (DAC) 202. A technique for accomplishing this is further discussed hereinbelow with reference to FIG. 3.

FIG. 2 illustrates a more purely digital implementation. In this case, the differencing and low pass filtering are performed digitally by the processing element 201. The implementation shown in FIG. 1 may be less expensive since the implementation shown in FIG. 2 may require an ADC of greater resolution and higher sampling rate.

To achieve good cancellation performance, it is desired to minimize the latency of the feedback loop (the time it takes for a signal to travel from the output of the processing element through the various elements and back to the output of the processing element). The latency should be a small fraction of the period of the sound being canceled, so that the cancellation signal is in phase with the external noise. That is, the cancellation circuit should react as quickly as possible to changes in the external noise, where the reaction delay requirement is set by the speed of change of the external noise. Higher audio frequencies require shorter delays. DAC 202 and ADC 207 will typically have dominant contributions to the latency. Many DACs and ADCs used for audio applications have latencies of several tens of microseconds or more and may not be suitable for use with the present invention. DACs and ADCs suitable for audio applications with latencies of a few microseconds or less are available. High latency DACs and ADCs may be applicable for use with the present invention if prediction techniques are used in the processing element 201. That is, the processing element predicts the future external noise based on previous samples and generates a cancellation signal which will be in phase with the future external noise by the time the cancellation signal passes through the DAC to the headphone 500. There are several prediction techniques known in the art.

Figure 3:
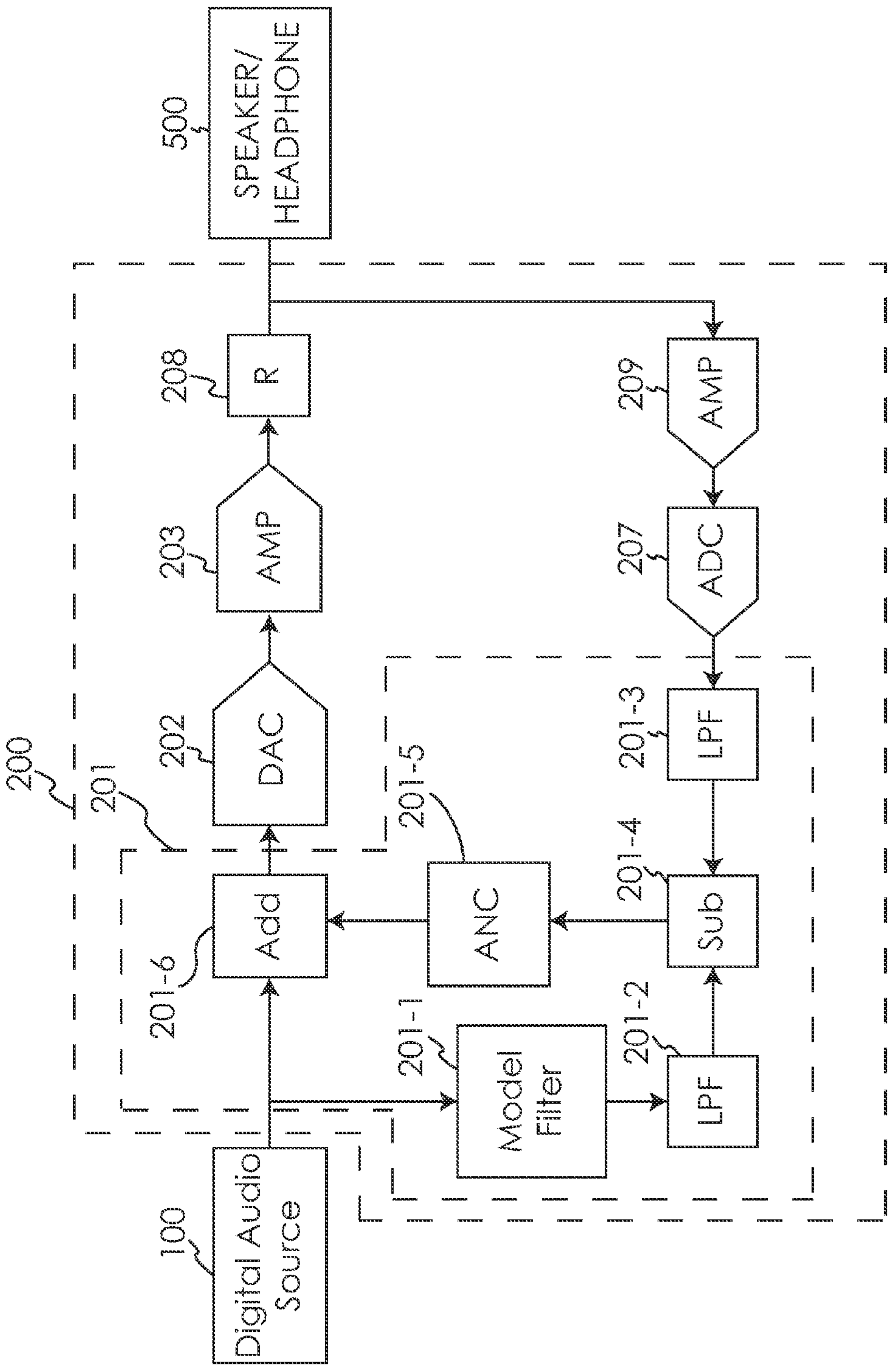
FIG. 3 is a schematic diagram depicting a further implementation of the present invention incorporating an adaptive modeling filter and series resistor.

FIG. 3 illustrates another embodiment of the present invention. Again, digital audio source 100 connects to a processing unit 201. Within processing unit 201, the input audio program material is connected to model filter 201-1 and one input of adder 201-6. The output of model filter 201-1 is passed through low pass filter 201-2 and connected to one input of subtractor 201-4. The output of subtractor 201-4 is passed through active noise cancellation unit 201-5 and directed to the remaining input of adder 201-6. The output of adder 201-6 passes through DAC 202 and connects to the input of amplifier 203. The output of amplifier 203 connects to a first terminal of series resister 208. The second terminal of series resistor 208 is connected both to headphone 500 and the input of amplifier 209. The output of amplifier 209 passes through ADC 207 and low pass filter 201-3 before being connected to the remaining input of subtractor 201-4 in a feedback loop.

As described hereinabove, it is difficult to perform noise cancellation on audio frequencies which have a corresponding period smaller than the time scale of the noise cancelling system. Therefore, low pass filtering is used to remove higher frequency signals and avoid instability in the system. However, low pass filtering components also introduce delay into the signal path, creating a tradeoff between the cutoff frequency of the low pass filters 201-2 and 201-3 and the performance of the system. DAC 202, ADC 207 and active noise cancellation unit 201-5 also introduce significant delay into the signal path. In the embodiment shown in FIG. 3, model filter 201-1 is a filter which reproduces the delaying effects of the components in the signal path including any gain and delay which may be frequency dependent. Ideally, the output of low pass filter 201-2 is identical to that portion of the output of low pass filter 201-3 representing the output of adder 201-6. The output signal of subtractor 201-4 therefore ideally consists of a digital signal representing the external noise signal to be cancelled. Active noise cancellation unit 201-5 uses an adaptive active noise control algorithm to create a cancelling signal which is then combined with the original source signal by adder 201-6. Many such noise control algorithms are known in the art, such as the Filtered-X LMS algorithm.

The embodiment of FIG. 3 also includes series resistor 208, which prevents the signal from headphone 500 acting as a microphone from being suppressed when amplifier 203 is implemented as a voltage output device, such as an operational amplifier. The value of series resistor 208 should be on the order of headphone 500, which is in the range of ten ohms to a few hundred ohms depending on the particular brand and model of headphones being used. Series resistor 208 can be implemented as a programmatically selectable resistance or can be of fixed value.

A typical headphone has the left and right channels sharing the ground connection which results in some small mixing of the left and right channels measured at the input of amplifier 209. This is because the headphone cable 502 has a non-zero resistance, typically much less than the headphone speaker. The amount of mixing is determined by the ratio of the cable resistance to the resistance of the speaker. This mixing can be incorporated into model filter 201-1. Model filter 201-1 should correspond to the characteristics of the value of series resistor 208 and the characteristics of headphone 500, which will change when the headphone 500 is changed and is generally not known in advance. This means that model filter 201-1 must be at least partially constructed adaptively. Several techniques to accomplish this are known in the art. For examples, see Kuo, Sen, and Morgan, Dennis, *Active Noise Control systems: Algorithms and DSP Implementations*. New York: Wiley, 1996.

Figure 4:
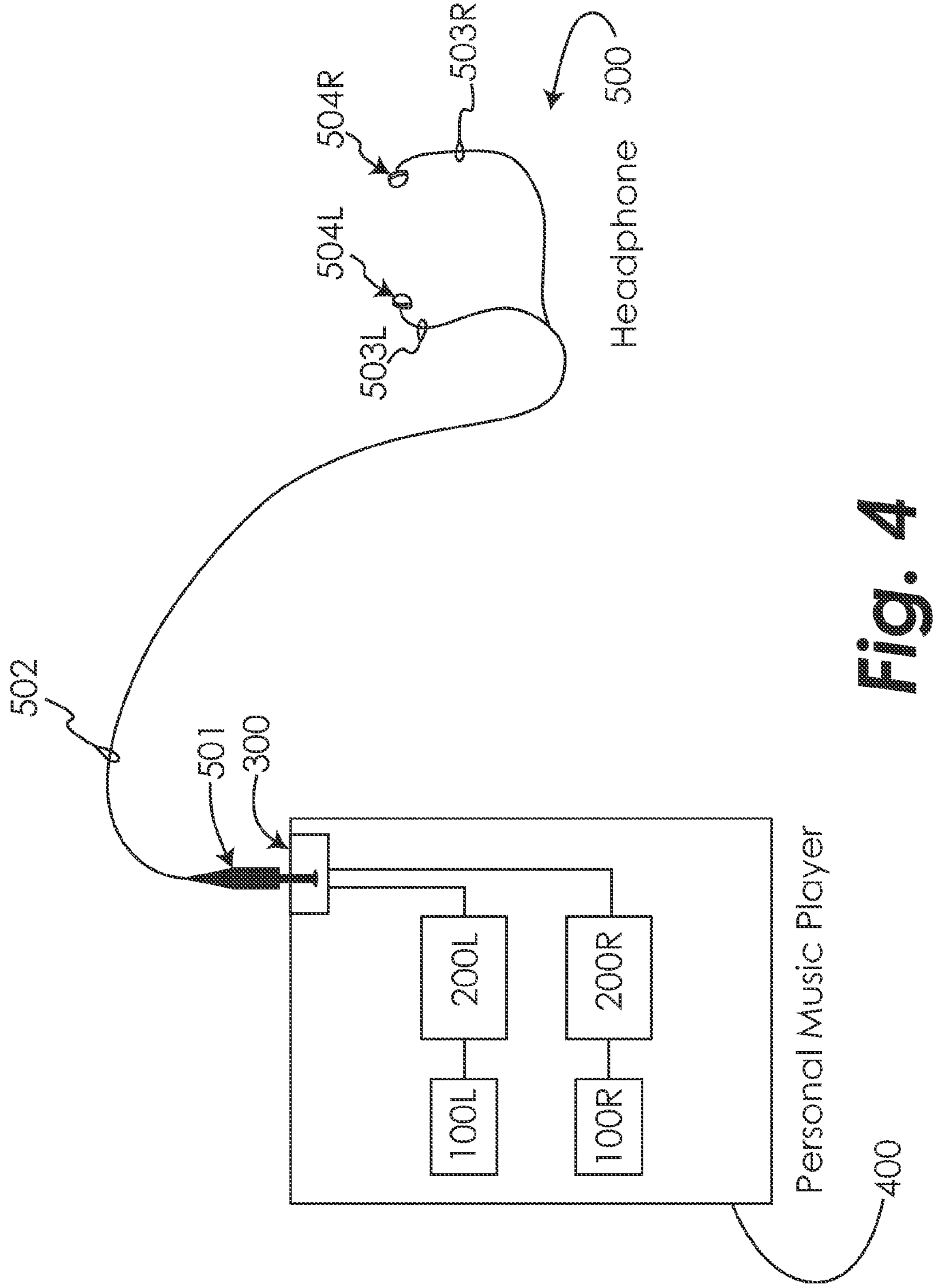
FIG. 4 is a schematic diagram depicting the present invention as incorporated into a personal music player.

FIG. 4 illustrates an embodiment of the present invention as incorporated into a personal music player 400. Two channels, left and right, are implemented as indicated by the "L" and "R" suffixes of various components. Personal music player 400 contains a digital audio source 100 for each audio channel. Digital audio source 100 provides input to control unit 200 which processes both the source signal and sensed external noise signal. The output of both control units 200L and 200R are connected to jack 300, into which a standard stereo headphone set 500 may be connected. Headphone connector 501 operatively couples the speakers 504L and 504R to music player 400 via cable 502. Cable 502 splits near the speakers, with one audio channel sent over each of cables 503L and 503R. For each audio channel, control unit 200 utilizes the corresponding speaker 504 as both an output driver and a noise-sensing microphone.

Figure 5:
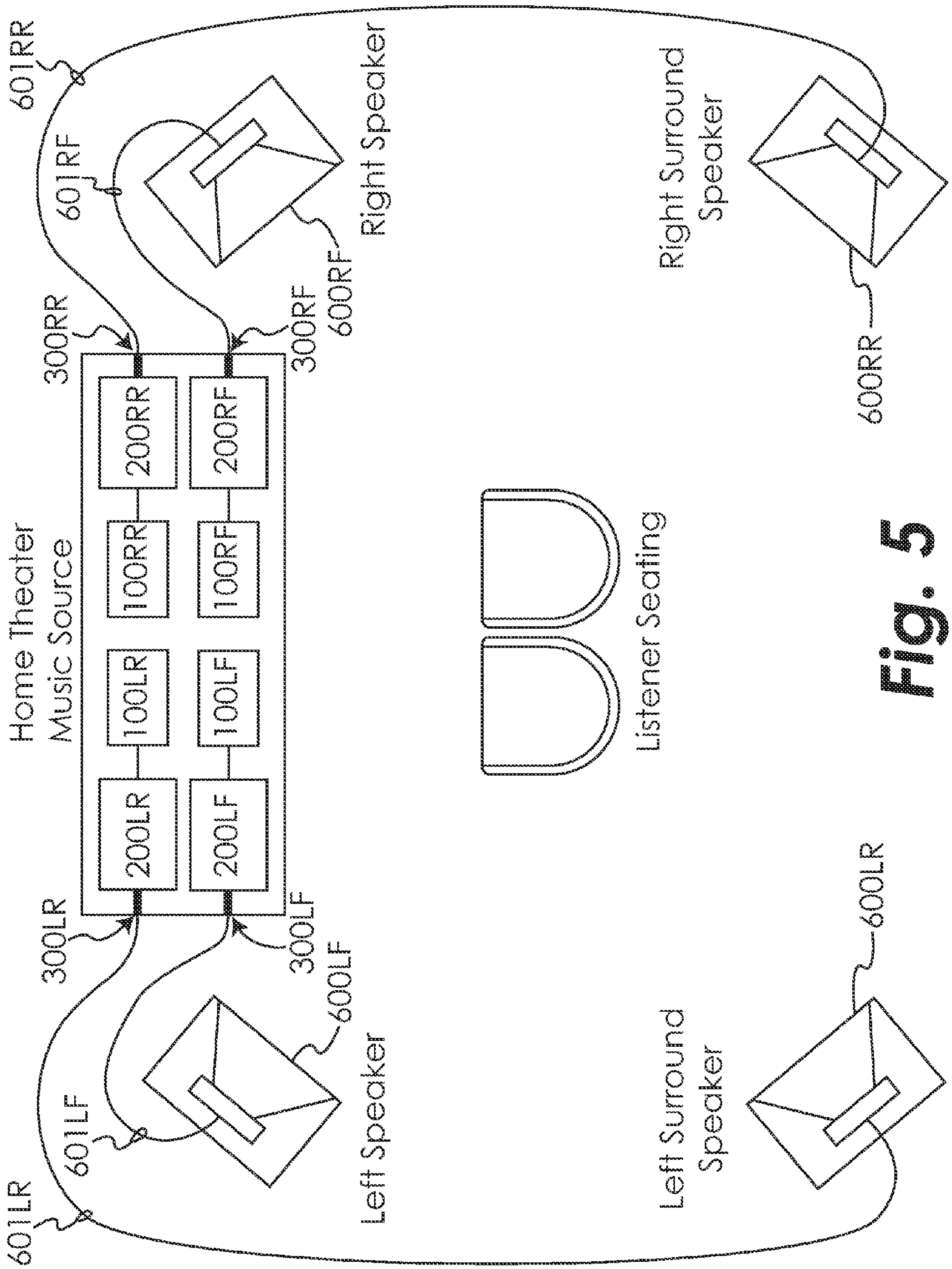
FIG. 5 is a schematic diagram depicting the present invention as incorporated into a home theater system.
Figure 6:
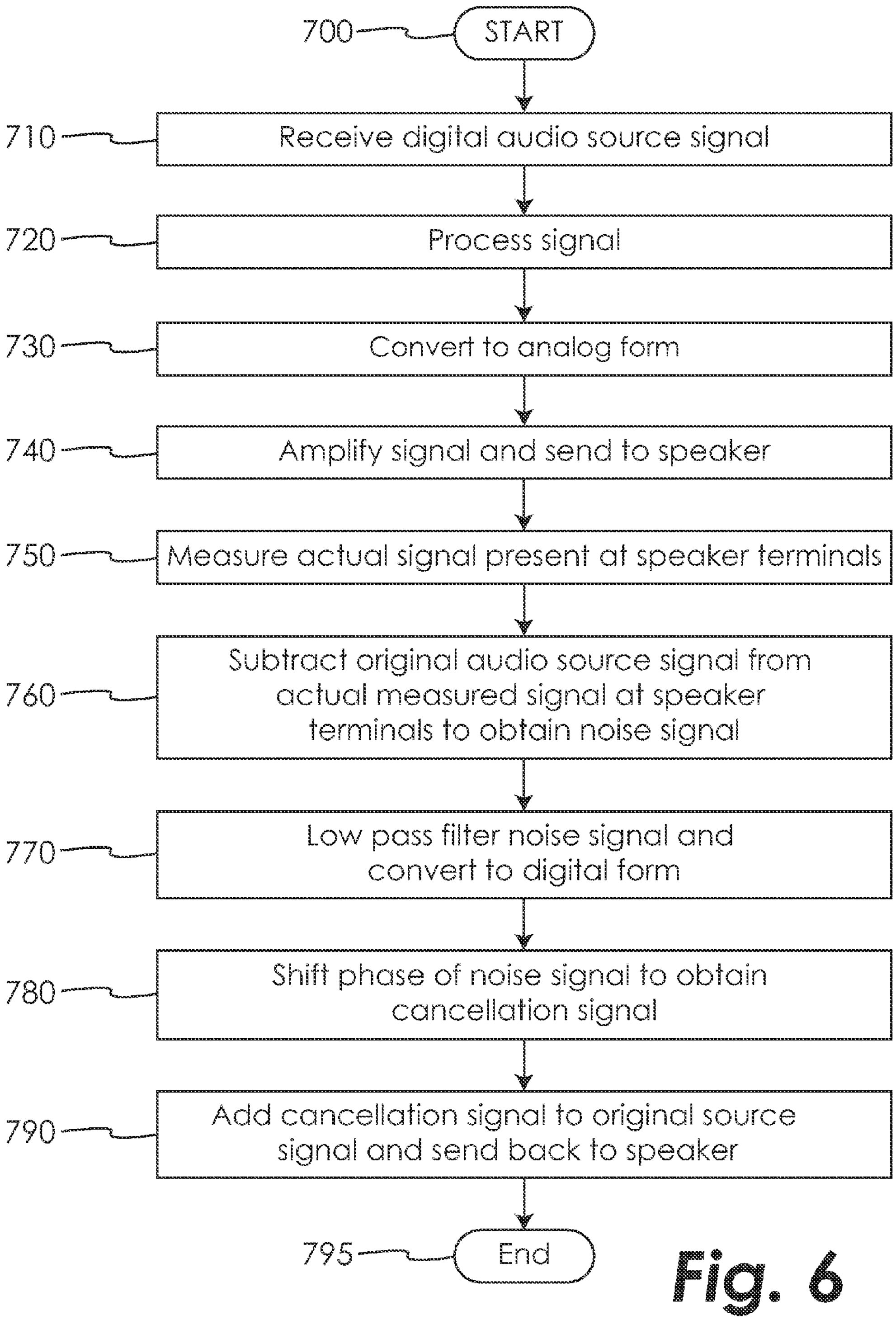
FIG. 6 is a flow diagram demonstrating one embodiment of the method claimed by the present invention.

FIG. 5 illustrates another embodiment of the present invention as incorporated in a home theater audio system. Again, a separate audio source 100 and control unit 200 are provided for each audio channel. In this example, four speakers 600 are shown, with suffixes LF, RF, LR, and RR indicating left-front, right-front, left-rear, and right-rear respectively. Each control unit 200 is connected to a connector 300, which operatively couples speaker 600 to control unit 200 via speaker cable 601, with each speaker 600 acting as both an output driver and noise sensing microphone. Furthermore, in this example, speakers 600 can be used not only to sense unwanted background noise from outside the listening room, but also to sense imperfections in the frequency response of the room itself. For example, a reference signal, such as white or pink noise, can be output to the speakers with the resulting room response again measured using the same speakers as microphones. The data from this operation can then be used to make equalization adjustments in the amplifier's output, as is known in the art FIG. 6 is a flow diagram illustrating the method of removing unwanted noise described hereinabove. The process begins at start point 700 where the digital source audio input is received (stage 710). The signal is then processed (stage 720) and converted to analog form (stage 730). After proper amplification, the signal is then sent to the speaker (stage 740). At stage 750, the system measures the actual signal present at the speaker terminals, which includes both the intended program signal and the noise signal. The original source signal is then subtracted from this measured signal to extract the noise signal component (stage 760). After low-pass filtering the noise signal and converting to digital form (stage 770), the noise signal is phase shifted substantially 180° (although other amounts of phase shift are contemplated by the present invention) to obtain a cancellation signal (stage 780) which is then added back to the original signal in a feedback loop and output to the speaker (stage 790), with the process ending at point 795.

While the invention has been illustrated and described in detail in the drawings and foregoing description, the same is to be considered as illustrative and not restrictive in character, it being understood that only certain embodiments have been shown and described and that all equivalents, changes, and modifications that come within the spirit of the inventions as described herein and/or by the following claims are desired to be protected.

Hence, the proper scope of the present invention should be determined only by the broadest interpretation of the appended claims so as to encompass all such modifications as well as all relationships equivalent to those illustrated in the drawings and described in the specification.

What is claimed is:

1. An active audio adjustment system comprising:

a processing unit which senses external sound using a speaker, wherein said speaker is also being used to output sound to the user, said speaker comprising a single electromechanical device that functions simultaneously as both an external noise sensing microphone to produce a noise signal and as an audio output driver;

wherein said external sound comprises unwanted background noise and wherein said processing unit performs an active cancelling function to create a reduction in the level of said unwanted background noise perceived by the user.

2. The system of claim 1, wherein said processing unit uses said external sound to make frequency equalization adjustments in the output to said speaker.

3. The system of claim 1, wherein said speaker comprises a headphone speaker.

4. An active audio noise cancellation system comprising:

a control unit which receives an input audio signal and is adapted to be connected to an external speaker at a connection point, said control unit providing at said connection point an output audio source signal to said external speaker and receiving at said connection point a noise signal from said external speaker, said speaker comprising a single electromechanical device that functions simultaneously as both an external noise sensing microphone to produce said noise signal and as an audio output driver;

wherein said control unit is operative to subtract said output audio source signal from a signal present at said connection point to obtain said noise signal, shifts the phase of the noise signal to obtain a cancellation signal, and outputs a combination of said input audio signal and said cancellation signal to said speaker, thereby reducing external noise perceived by a user.

5. The system of claim 4, further comprising:

a coupler for coupling the control unit to said speaker.

6. The system of claim 5, wherein the phase of said noise signal is shifted 180 degrees.

7. The system of claim 5, wherein said control unit comprises:

a processing unit which receives said input audio signal and outputs a third signal consisting of a combination of said input audio signal and said cancellation signal;

a digital to analog converter which converts said third signal to analog form and outputs the result as a fourth signal;

a first amplifier which amplifies said fourth signal and outputs the result as a fifth signal;

a second amplifier which amplifies said fourth signal, wherein the output of said second amplifier is connected to said connection point;

a first difference amplifier which subtracts said fifth signal from said signal present at said connection point and outputs the result as a seventh signal;

a first low pass filter which filters said seventh signal and outputs the result as an eighth signal; and an analog to digital converter that converts said eighth signal to digital form and outputs the result as a ninth signal to said processing unit;

wherein said processing unit shifts the phase of said ninth signal to produce said cancellation signal.

8. The system of claim 5, wherein said control unit comprises:

a processing unit which receives said input audio signal and outputs a third signal consisting of a combination of said input audio signal and said cancellation signal;

a digital to analog converter which converts said third signal to analog form and outputs the result as a fourth signal;

a first amplifier which amplifies said fourth signal, wherein the output of said first amplifier is connected to said connection point; and an analog to digital converter that converts a seventh signal present at the connection point to digital form and outputs the result as an eighth signal to said processing unit.

9. The system of claim 8, wherein said processing unit includes a modeling filter which substantially compensates for delays caused by components in said control unit.

10. The system of claim 8, further comprising:

a resistor;

wherein said resistor is connected between said first amplifier and said connection point to prevent suppression of a microphonic component of said seventh signal when said first amplifier is implemented as a voltage output device.

11. The system of claim 5, wherein said speaker comprises a headphone speaker.

12. A method comprising the steps of:

utilizing a single speaker to both sense external sound and output a desired audio signal in an active audio adjustment system, said speaker comprising a single electromechanical device that functions simultaneously as both an external noise sensing microphone to produce a noise signal and as an audio output driver;

wherein said external sound comprises unwanted background noise and wherein said active audio adjustment system is an active noise cancellation system.

13. The method of claim 12, wherein said external sound is being used to make frequency equalization adjustments in the output to said speaker.

14. The method of claim 12, wherein said speaker is a headphone speaker.

15. A method comprising the steps of:

receiving a first audio signal;

receiving a second audio signal from a speaker, said speaker comprising a single electromechanical device that functions simultaneously as both an external noise sensing microphone to produce a noise signal and as an audio output driver;

processing said first and second audio signals to extract said noise signal which approximates the external noise being sensed by said speaker;

shifting the phase of said noise signal to obtain a third signal;

outputting a combination of said first and third signals to said speaker, thereby reducing the external noise perceived by a user.

16. The method of claim 15, wherein said first audio signal is output from a digital audio source.

17. The method of claim 15, wherein said speaker comprises a headphone speaker.

18. The method of claim 15, wherein said phase shift is 180 degrees.

* * * * *